United States Patent
Brems et al.

(10) Patent No.: US 10,369,775 B2
(45) Date of Patent: Aug. 6, 2019

(54) METHOD OF RELEASING GRAPHENE FROM SUBSTRATE

(71) Applicants: IMEC VZW, Leuven (BE); Katholieke Universiteit Leuven, Leuven (BE)

(72) Inventors: Steven Brems, Kessel-Lo (BE); Cedric Huyghebaert, Heverlee (BE); Ken Verguts, Leuven (BE); Stefan De Gendt, Wijnegem (BE)

(73) Assignees: IMEC vzw, Leuven (BE); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 15/836,737

(22) Filed: Dec. 8, 2017

(65) Prior Publication Data

US 2018/0162115 A1 Jun. 14, 2018

(30) Foreign Application Priority Data

Dec. 9, 2016 (EP) ..................................... 16203166

(51) Int. Cl.
*B32B 43/00* (2006.01)
*C01B 32/194* (2017.01)
(Continued)

(52) U.S. Cl.
CPC ............ *B32B 43/006* (2013.01); *B32B 9/007* (2013.01); *B32B 15/04* (2013.01); *B32B 37/025* (2013.01); *C01B 32/184* (2017.08); *C01B 32/194* (2017.08); *C07F 7/081* (2013.01); *C07F 7/10* (2013.01); *C25F 5/00* (2013.01); *B32B 37/00* (2013.01); *B32B 37/18* (2013.01);

(Continued)

(58) Field of Classification Search
CPC ...... B32B 38/10; B32B 43/006; B32B 37/925; B32B 37/00; B32B 37/18; C01B 32/184; C01B 32/194; C01B 31/0484; C01B 31/0438; C01B 31/0453; C25F 5/00; B81C 1/00; Y10T 156/11; Y10T 156/19
USPC .................................................. 156/701, 750
See application file for complete search history.

(56) References Cited

U.S. PATENT DOCUMENTS 8,431,103 B2 * 4/2013 Song ...................... B82Y 30/00
216/52
8,877,572 B2 * 11/2014 Lee ......................... B82Y 30/00
438/158

(Continued)

FOREIGN PATENT DOCUMENTS

EP          2 719 797          3/2016

*Primary Examiner* — Mark A Osele
*Assistant Examiner* — Nickolas R Harm
(74) *Attorney, Agent, or Firm* — Knobbe, Martens, Olson & Bear LLP

(57) ABSTRACT

The disclosed technology generally relates to preparing two-dimensional material layers, and more particularly to releasing a graphene layer from a template substrate. According to an aspect, a method of releasing a graphene layer includes providing a template substrate on which the graphene layer is provided, the method comprising: subjecting the graphene layer and the template substrate to a water treatment by soaking the graphene layer and the template substrate in water such that water is intercalated between the template substrate and the graphene layer; and subjecting the graphene layer and the template substrate to a delamination process, thereby releasing the graphene layer from the template substrate.

17 Claims, 4 Drawing Sheets

(51) Int. Cl.
  *C01B 32/184* (2017.01)
  *B32B 9/00* (2006.01)
  *B32B 15/04* (2006.01)
  *B32B 37/00* (2006.01)
  *C07F 7/08* (2006.01)
  *C07F 7/10* (2006.01)
  *C25F 5/00* (2006.01)
  *B32B 38/10* (2006.01)
  *B81C 1/00* (2006.01)
  *B32B 37/18* (2006.01)

(52) U.S. Cl.
  CPC .......... *B32B 38/10* (2013.01); *B32B 2311/06* (2013.01); *B81C 1/00* (2013.01); *C01B 2204/02* (2013.01); *Y02P 20/582* (2015.11); *Y10T 156/11* (2015.01); *Y10T 156/19* (2015.01)

(56) References Cited

U.S. PATENT DOCUMENTS

| | | | |
|---|---|---|---|
| 9,039,886 B2* | 5/2015 | Gong | B32B 38/10 156/153 |
| 9,169,575 B1* | 10/2015 | Bedworth | C25D 1/14 |
| 9,427,946 B2* | 8/2016 | Willner | H01L 21/0201 |
| 2014/0231270 A1* | 8/2014 | Loh | C25F 5/00 205/674 |
| 2014/0238873 A1* | 8/2014 | Li | C25F 5/00 205/644 |
| 2014/0308523 A1* | 10/2014 | Veerasamy | B82Y 30/00 428/408 |
| 2016/0137507 A1* | 5/2016 | You | C01B 31/0438 428/408 |
| 2016/0344035 A1* | 11/2016 | Zhamu | H01M 4/628 |
| 2017/0114450 A1* | 4/2017 | Babenko | C23C 16/003 |

\* cited by examiner

METHOD OF RELEASING GRAPHENE FROM SUBSTRATE

CROSS-REFERENCE TO RELATED APPLICATIONS

This application claims foreign priority to European Patent Application No. EP 16203166, filed Dec. 9, 2016, the content of which is incorporated by reference herein in its entirety.

BACKGROUND

Field

The disclosed technology generally relates to preparing two-dimensional material layers, and more particularly to releasing a graphene layer from a template substrate.

Description of the Related Technology

There is considerable interest in developing circuits and devices two-dimensional or layered materials, such as graphene. In some processes, one or more graphene layers, each having a substantially 2D structure, may be formed on a template substrate, for instance by chemical vapor deposition (CVD). The graphene layer(s) are then to be released or delaminated from the template substrate and transferred to a target substrate.

EP 2 719 797 discloses a graphene transfer method wherein graphene is synthesized on an initial substrate. The graphene is released from the substrate using an electrolysis process. The released graphene is subsequently bonded to a target substrate.

However, both the separation and the transfer of a graphene layer remain challenging and process variations may result in unreliable circuits or devices when integrated using some graphene layers formed using existing methods. Thus, there is a need for improved preparation method such as graphene that is simpler and higher quality for integration in circuits or devices.

SUMMARY OF CERTAIN INVENTIVE ASPECTS

An objective of the disclosed technology is to provide an improved method of releasing a graphene layer from a template substrate, enabling more reliable separation of the graphene layer. Additional or alternative objectives may be understood from the following.

According to a first aspect of the disclosed technology there is provided a method of releasing a graphene layer from a template substrate on which the graphene layer is provided, the method comprising: subjecting the graphene layer and the template substrate to a water treatment by soaking the graphene layer and the template substrate in water such that water is intercalated between the template substrate and the graphene layer; and subjecting the graphene layer and the template substrate to a delamination process, thereby releasing the graphene layer from the template substrate.

As realized by the inventors, soaking the graphene layer and the template substrate in liquid phase water such that water is intercalated between the template substrate and the graphene layer enables a more reliable separation, i.e. delamination, of the graphene layer from the template substrate. The intercalated water between the template substrate and the graphene layer allows separation by applying a smaller separation force to the graphene layer and the template substrate during the delamination process compared to the prior art. The intercalated water also reduces risk of damaging graphene layer during the delamination process.

By delamination process is hereby meant a process adapted to drive a release of the graphene layer from the template substrate. The graphene layer may be bonded to the template substrate by adhesion. The graphene layer may be bonded to the template substrate by Van der Waal forces. The delamination process is in other words a process adapted to break the bonding between the graphene layer and the template substrate. By releasing or delaminating the graphene layer from the template substrate the graphene layer may be separated from the template substrate. The process may include supplying energy to the graphene layer and the template substrate in a form driving the release of the graphene layer from the template substrate. Advantageous delamination process will be further described below and may include supplying the energy by means of bubble formation in a liquid, electrolysis and/or ultrasound.

By intercalation of water between the template substrate and the graphene layer is hereby meant a process wherein the water (in which the graphene layer and the template substrate is submerged) enters between the graphene layer and the template substrate. The intercalated water may form one to a few (mono-)layers of water. The intercalated water may also be referred to as interfacial water (IFW).

The soaking may be of a duration allowing intercalated water to form along at least a sufficient portion of the interface between the graphene layer and the template layer. A sufficient portion may here be understood as a portion which is sufficient for allowing separation of the graphene layer from the template substrate with no or a minimum risk of damaging the graphene layer. Preferably, the soaking may be of a duration allowing intercalated water to form along a major portion of the interface between the graphene layer and the template layer. More preferably, the soaking may be of a duration allowing intercalated water to form along the entire interface between the graphene layer and the template layer. This may facilitate releasing the graphene layer from the template substrate.

According to one embodiment the graphene layer and the template substrate are subjected to the water treatment by soaking for a predetermined duration prior to initiating the delamination process. Thus, intercalated water may be formed between the graphene layer and the template layer prior to subjecting the graphene layer and the template layer to the conditions of the delamination process. This may improve the overall efficiency of the separation method and reduce the risk of damaging the graphene layer.

However, it is also possible to apply the water treatment and the delamination process with an overlap. For instance, the graphene layer and the template layer may be subjected to the delamination process at a reduced power (e.g., a lower rate of bubble formation, a lower bias driving the electrolysis, reduced power of the ultrasound).

The graphene layer and the template substrate may be subjected to the water treatment by soaking for a predetermined duration of at least 1 hour. An extended duration of the soaking enables intercalation of water along a greater portion of the interface between the graphene layer and the template substrate. Correspondingly, an extended duration enables intercalation of water along the entire interface between the graphene layer and the template layer also for graphene layers of increased lateral/in-plane dimensions.

The water may be heated to a temperature of at least 30° C., at least 50° C., or at least 80° C. Heating the liquid phase water provides thermal energy which may accelerate the intercalation process. An overall time efficiency of the separation method may thereby be improved.

In any case, the water is preferably heated to a temperature below the boiling point. Bubble formation prior to a sufficient water intercalation has occurred may thereby be avoided.

The water treatment may include soaking the graphene layer and the template substrate by submerging the graphene layer in the liquid phase water.

In addition to said water treatment and said delamination process, the method may further include transferring and bonding of the graphene layer to a target substrate.

According to one embodiment, the method further comprises: transferring the template substrate and the graphene layer to a target substrate and bonding the graphene layer to the target substrate; and subsequent to said transferring and bonding, subjecting the template substrate and the graphene layer to said delamination process wherein the graphene layer is released from the template substrate and remains bonded to the target substrate.

This method does not require any additional temporary handling wafer between the delamination process and the transfer and bonding. Obviating the need of a temporary additional handling wafer reduces the risk of contaminating the graphene layer during processing relating to bonding and release from such a temporary wafer. The method also enables reuse of the template substrate.

The transfer process may be performed prior to or subsequent to the water treatment. A bonding process for bonding the graphene layer to the target substrate may be performed prior to the water treatment. The bonding process may alternatively be performed subsequent to the water treatment. The bonding process may alternatively be performed with an overlap with respect to the water treatment. Accordingly, the bonding may be achieved during the water treatment.

By transferring the graphene layer to the target substrate is hereby meant bringing a first (main) surface of the graphene layer in contact with a (main) surface of the target substrate. The graphene layer is provided on the template substrate with a second (main) surface (opposite the first surface) of the graphene layer in contact with a (main) surface of the template substrate. Accordingly, the transfer includes forming of a stack including the target substrate, the graphene layer and the template substrate.

The graphene layer and the target substrate may be bonded by dry bonding. Hence no intermediate layers are needed between the graphene layer and the hydrophobic surface of the target substrate. The graphene layer may be bonded by applying a pressure to press the graphene layer against the target substrate.

The graphene layer may be bonded to a hydrophobic surface of the target substrate. By virtue of the hydrophobic surface of the target substrate, water intercalation between the target substrate and the graphene layer may be counteracted.

The hydrophobic surface may be formed by a self-assembled monolayer (SAM) on the target substrate. The SAM may include a hydrophobic terminal group or tail group. The head group of the SAM may be selected to allow bonding thereof to the target substrate.

An alternative method embodiment including transfer and bonding of the graphene layer further comprises: forming a carrier layer on a second surface of the graphene layer facing away from the template substrate; and subsequent to releasing the graphene layer from the template substrate, transferring and bonding the graphene layer to a target substrate with a first surface of the graphene layer facing the target substrate.

This embodiment allows a graphene layer to be transferred and bonded to a target substrate. The carrier layer allows protection of the second surface of the graphene layer during the delamination process. The carrier layer may further reduce the risk of cracking or folding of the graphene layer during the delamination. The carrier layer may also act as protection for the graphene layer and facilitate handling of the graphene layer after the delamination process, for instance during the transfer of the graphene layer to the target substrate.

The forming of the carrier layer may be performed prior to or subsequent to said water treatment.

Subsequent to the bonding, the carrier layer may be removed from the second surface, wherein the graphene layer remains on the target substrate.

By transferring the graphene layer to the target substrate is hereby meant bringing the first (main) surface of the graphene layer in contact with a (main) surface of the target substrate. Accordingly, the transfer includes forming of a stack including the target substrate and the graphene layer. Subsequent to forming the carrier layer, also the carrier layer forms part of the stack.

The graphene layer and the target substrate may be bonded by dry bonding. Hence no intermediate layers are needed between the graphene layer and the target substrate. The graphene layer may be bonded by applying a pressure to press the graphene layer against the target substrate.

The carrier layer may be a spin-coated organic layer. The carrier layer may be a spin-coated polymer-including layer. Spin-coating allows controlled forming of a carrier layer as a thin film with good coverage and a high degree of thickness control.

As discussed above, various delamination processes are possible:

The delamination process may include submerging the template substrate and the graphene layer in a liquid and forming bubbles at the interface between the template substrate and the graphene layer. Bubbles forming at the interface may drive the release of the graphene layer from the template substrate.

The delamination process may include subjecting the template substrate and the graphene layer to electrolysis. Electrolysis allows convenient and accurate control of the resulting separation forces between the template substrate and the graphene layer by controlling the bias applied across the electrodes. By the electrolysis bubbles may form at the interface between the graphene layer and the template substrate.

The template substrate and the graphene layer may be submerged in a liquid forming an electrolyte. A bias may be applied by a voltage source across a first electrode and a second electrode submerged in the liquid.

The delamination process may include subjecting the template substrate and the graphene layer to ultrasound. By the resulting pressure waves bubbles may form at the interface between the graphene layer and the template substrate.

The template substrate and the graphene layer may be submerged in a liquid. Ultrasonic signals may be induced in the liquid. The ultrasonic signals may be ultrasonic pulses.

The liquid in which the graphene layer and the template substrate may be submerged during the delamination process, as set out above, may be formed by the water used in the water treatment. In other words, the water in which the graphene layer and the template substrate are soaked such that that water is intercalated between the template substrate and the graphene layer. Hence, the water treatment and the delamination process need not be performed at different and physically separate processing equipment but may be performed at a same location. For instance, the water treatment and the delamination process may be performed in a same water-including container or tank.

The graphene layer may be grown on the template substrate. The template substrate may also be referred to as a growth substrate. Graphene layer may be epitaxially grown on the template substrate. The graphene layer may be grown by CVD.

The surface of the template substrate on which the graphene layer is provided may be formed by a transition metal, an alloy of transition metals, a group III element or a group IV element. There exist growth processes enabling forming of high-quality graphene layers on such template substrates.

The surface of the template substrate may be formed by Platinum (Pt). Pt is an advantageous material for CVD-based graphene growth and allows high quality growth of both monolayer graphene and millimeter-sized graphene islands. Pt has a comparably low tendency to oxidize during the water treatment. Oxidization may otherwise reduce the rate at which intercalation occurs during the water treatment. Pt also allows the template substrate to be used as an electrode during an electrolysis-based delamination process.

The template substrate may include a growth layer on which the graphene layer is provided and a support layer on which the growth layer is arranged. The growth layer may be formed of any of the aforementioned materials and with a thickness on the order of nanometers to hundreds of nanometers. The growth layer may be formed by a foil any of the aforementioned materials. The support layer may support the growth layer. The support layer may be a sapphire layer. The support layer may be an MgO layer. The support layer may be a stack of a Si-layer and an MgO-layer. The support layer may be an $Al_2O_3$-layer. Such support layers enable template substrates with a surface (i.e. of the growth layer) of 111-, 100- and 110-orientation.

It has been further realized by the inventors that intercalation (between a graphene layer and a template substrate) of other liquids than water also may enable a more reliable separation, i.e. delamination, of the graphene layer from the template substrate, compared to prior art approaches.

Thus, according to a second aspect of the disclosed technology there is provided a method of releasing a graphene layer from a template substrate on which the graphene layer is provided, the method comprising: subjecting the graphene layer and the template substrate to a liquid treatment by soaking the graphene layer and the template substrate in a liquid such that liquid is intercalated between the template substrate and the graphene layer; and subjecting the graphene layer and the template substrate to a delamination process, thereby releasing the graphene layer from the template substrate.

As discussed in connection with the first aspect, the liquid treatment may advantageously be a water treatment wherein the liquid may be liquid phase water. However, the liquid may more generally be a liquid of molecules with a dipole moment and having a molecular size comparable to that of water.

According to one embodiment the liquid may be (liquid phase) chloroform. By soaking the graphene layer and the template substrate in chloroform the chloroform may intercalate between the template substrate and the graphene layer. This enables a more reliable separation, i.e. delamination, of the graphene layer from the template substrate.

The details and variations discussed in connection with the method of the first aspect apply correspondingly to the method of the second aspect. For instance, the graphene layer and the template substrate may be subjected to the liquid treatment for a predetermined duration of at least 1 hour. The liquid may be heated (e.g., to a temperature above room temperature but below the boiling point of the liquid) to accelerate the intercalation process. The graphene layer may further be transferred to a target substrate according to any of the above described embodiments.

BRIEF DESCRIPTION OF THE DRAWINGS

The above, as well as additional objects, features and advantages of the disclosed technology, will be better understood through the following illustrative and non-limiting detailed description of preferred embodiments of the disclosed technology, with reference to the appended drawings. In the drawings like reference numerals will be used for like elements unless stated otherwise.

FIGS. 4a-4c are scanning electron microscope (SEM) images of a Pt foil/graphene layer before growth and after a water treatment.

DETAILED DESCRIPTION OF CERTAIN ILLUSTRATIVE EMBODIMENTS

Detailed embodiments of the present inventive concept will now be described with reference to the drawings.

A method of releasing a graphene layer 114 from a template substrate 112 will to be described with reference to FIGS. 1a-1c.

Figure 1A:
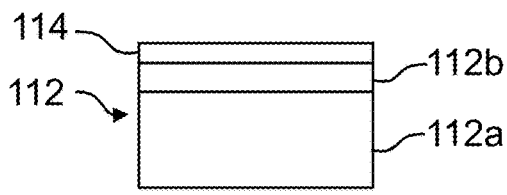
FIGS. 1a-1c are schematic illustrations of intermediate structures at various stages of a method of releasing a graphene layer from a template substrate, according to embodiments.
Figure 1B:
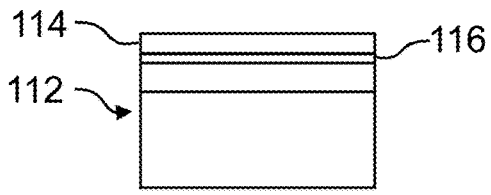

FIG. 1a illustrates an intermediate structure having the graphene layer 114 provided on the template substrate 112. The template substrate 112 may include a support layer 112a and a growth layer 112b. The growth layer 112b forms the main surface of the template substrate 112 on which the graphene layer 114 is provided. The growth layer 112b is arranged on the support layer 112a.

The growth layer 112b may comprise or be formed of a foil of a metal, e.g., a transition metal, for instance Pt, Cu, Jr or Ni. The support layer 112a may comprise or be formed of an insulator, e.g., a sapphire layer, according one embodiment. The support layer 112a may comprise or be formed of an MgO layer, according to another embodiment. The support layer 112a may comprise or be a stack including a Si-layer and an MgO-layer, according to another embodiment. The support layer 112a may be or formed of an $Al_2O_3$-layer, according to yet another embodiment. The growth layer 112b may be formed with a 111-, 100- or 110-orientation on the support layer 112a. In implementations where no particular crystallinity is provided in the support layer 112b, the support layer 112b may also comprise or be a stack of a Si-layer and a $SiO_2$-layer. According to a further option, the template substrate 112 may be formed of a group III or group IV semiconductor substrate. Examples include a template substrate comprising a stack of Si(111)/Ge(111), a stack of Si(100)/Ge(100), a bulk Ge wafer or a stack of sapphire(0001)/GaN.

The surface of the template substrate 112 on which the graphene layer 114 is provided represents a main surface of the template substrate 112. The main surface of the template substrate 112 may be referred to as a first or upper surface of the template substrate 112. In FIG. 1a, the main surface of the template substrate 112 is formed by the growth layer 112b.

The surface of the graphene layer 114 facing away from template substrate 112 represents a first main surface of the graphene layer 114. The first main surface of the graphene layer 114 may be referred to as a first surface of the graphene layer 114. The surface of the graphene layer 114 facing the template substrate 112 represents a second main surface of the graphene layer 114. The second main surface of the graphene layer 114 may be referred to as a second surface of the graphene layer 114.

It should be noted that the drawings show the layer structures in a schematic manner. The dimensions of the various layers, e.g., the relative thicknesses of the layers as illustrated, may differ actual relative thicknesses in a physical structure. In addition, the lateral dimensions of the template substrate 112 may be greater than those of the graphene layer 114 in some implementations, such that one or more graphene layers are formed on portions of a main surface of the template substrate 112.

The graphene layer 114 may be epitaxially grown on the main surface of the template substrate 112 in a CVD process, according to some embodiments. The growth layer 112b may act as a catalyst during the CVD process. Other options include epitaxially growing a graphene layer by heating a SiC template substrate.

The method of releasing a graphene layer according to embodiments comprises subjecting the graphene layer 114 and the template substrate 112 to a water treatment by soaking the graphene layer 114 and the template substrate 112 in water. The result of the water treatment is illustrated with respect to an intermediate structure illustrated in FIG. 1b, where interfacial water 116 is intercalated between the template substrate 112 and the graphene layer 114.

The stack including the graphene layer 114 and the template substrate 112 may be submerged in water in a container or tank (not shown). The water used in the water treatment may be de-ionized water. The water may be ultra-pure water. De-ionized, and to an even greater extent, ultra-pure water may result in a reduced occurrence of contaminations on the graphene layer 114. The water may, however, also be an aqueous solution. The solution may include dissolved salt. The water may be aqueous NaCl, NaOH or KOH. A compound dissolved in the water may accelerate the intercalation process. For instance, the organization of the water molecules around dissolved ions (such as Na+ or K+) may facilitate the intercalation process.

The graphene layer 114 and the template substrate 112 may be submerged in the water for a duration which is sufficient for allowing intercalated water to form along at least a sufficient portion of the interface between the graphene layer 114 and the template layer 112. The minimum duration for this to occur may be dependent on factors such as the dimensions of the graphene layer 114, the particular composition of the water and the temperature of the water.

The minimum duration for obtaining a sufficient degree of the interfacial water 116 may be determined experimentally. For instance, by submerging a sample stack including a graphene layer 114 and a template substrate 112 for gradually increasing durations and inspecting the stack, e.g., by scanning electron microscopy (SEM), to determine the presence of interfacial water 116

As described herein, intercalation refers to inclusion or insertion of atoms, molecules between adjacent layers of materials. Thus, intercalated interfacial water in graphene refers to water inserted or included between adjacent layers of graphene or a layer of graphene and another material. Under some circumstances, intercalation of water molecules may expand the gap between the adjacent layers of materials. Because intercalated interfacial water molecules are not directly exposed to atmosphere, when subjected to an atmosphere under which exposed liquid water would normally evaporate, the water intercalate interfacial molecules may be removed at a substantially slower rate compared to exposed liquid water or water molecules that are adsorbed on a surface. Thus, the presence of intercalated interfacial water 116 may be distinguished from water adsorbed to the main surface of the graphene layer 114 facing away from the template substrate 112 since adsorbed water is typically removed by an annealing process, whereas intercalated interfacial water is removed at a much slower rate or substantially not removed. Hence, for the purpose of establishing a minimum duration of the soaking, the stack may be inspected by SEM after subjecting the stack to an anneal step, for instance at 500° C. for an hour or longer.

Once established for the sample, the predetermined minimum duration may be used for water treatment of stacks including a graphene layer 114 and a template substrate 112 of a configuration corresponding to that of the sample stack.

The graphene layer 114 and the template substrate 112 may be subjected to the water treatment by soaking for a predetermined duration of at least 1 hour.

To accelerate the intercalation process, the water may be heated to a temperature above room temperature. The water may be heated by heating coils arranged in the tank or an immersion heater. The water may be heated to a temperature of at least 30° C., at least 50° C., or at least 80° C. An elevated water temperature may allow a sufficient amount of intercalated water to form between the graphene layer 114 and the template substrate 112 in a time span even shorter than 1 hour. Especially, if the graphene layer 114 is grown to present an in-plane/lateral dimension on the order of only one to a few millimeters, or less than one millimeter.

A scanning electron microscopy (SEM) image of a Pt foil/graphene layer sample stack immediately after growth is shown in FIG. 4a. The observed color contrast corresponds mainly to different Pt grain orientations, which is related to an electron channeling contrast. The electron channeling contrast is formed as a result of electron backscattering effects which occur in a thin layer at the sample surface, which makes it a surface sensitive technique. When the electron beam penetrates further into the Pt foil, elastic scattering effects decollimate the electron beam and inelastic scattering reduces the energy of the electrons. When the electron beam penetrates the foil, the initially highly collimated beam, which is sensitive to the orientation of the Pt grains, is decollimated. Further scattering effects lead to the development of the bulk backscattering contribution, which is insensitive to crystal orientation, since the beam electron trajectories are effectively randomized. A few multilayer graphene spots are also visible in FIG. 4a and are indicated with dashed lines.

After submerging the sample stack for 16 h in 50° C. ultra-pure water, the electron channeling contrast of the different Pt grains is not visible anymore due to the intercalated interfacial water (IFW) layer, but the topography contrast arising from the network of Pt grain boundaries can still be observed (see FIGS. 4b, 4c). Some of the Pt grain boundaries are indicated with dashed lines for visibility in FIG. 4c.

Figure 4D:
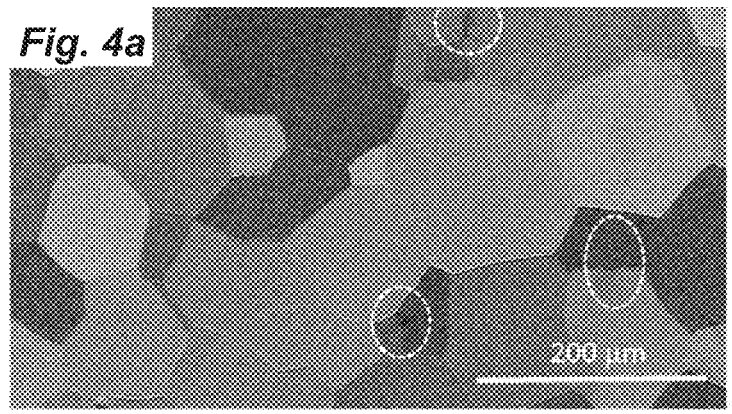
FIG. 4d is a Raman spectrum of a Pt foil/graphene layer before growth and after a water treatment.
Figure 4D:
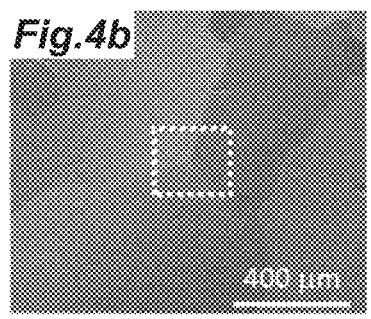
Figure 4D:
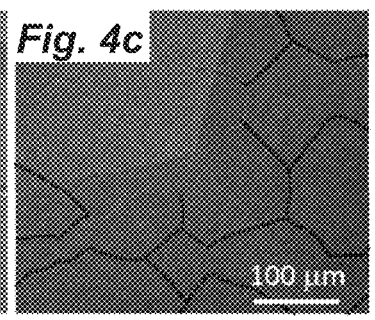
Figure 4D:
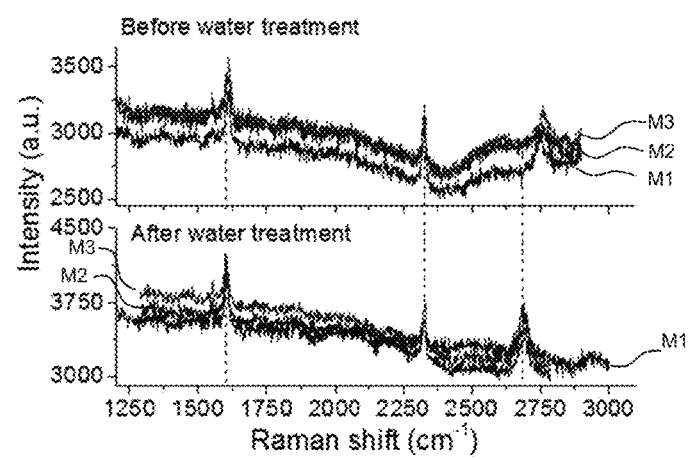

FIG. 4d shows results of Raman spectroscopy measurements performed immediately after graphene growth is (shown on top) and after the water treatment (shown below). Three measurements M1, M2, M3 were performed at different locations of the graphene layer before and after the water treatment. The width of the Raman spot was approximately 1 μm. In each of the measurements, the three pronounced peaks are visible, namely the D, G, and 2D peak. The D-peak, also called defect peak, is only present when the graphene layer is defective. The G and 2D peak corresponds with oscillations of the carbon atoms in the graphene sheet. The peak position, the full width half maximum and the peak ratios give information of graphene layer thickness (number of graphene layers), doping level of the graphene sheet, strain in the layer, stacking of the layers etc. The Raman spectroscopy shows a clear blue shift of the G and 2D peaks. The small additional Raman peak at 2328 $cm^{-1}$ is coming from $N_2$ present in air. The results show that after the water treatment, graphene is still present on the surface, but IFW is intercalated between the Pt foil and the graphene layer. Similar results have been obtained with a duration of the water treatment of about 3 hours with a water temperature of 80° C.

Figure 1C:
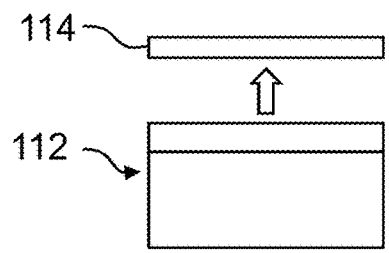

With reference to FIG. 1c, subsequent to the water treatment, the graphene layer 114 and the template substrate 112 are subjected to a delamination process. The delamination process includes subjecting the intermediate structure in FIG. 1b to a suitable form of energy, e.g., chemical, electrochemical or mechanical energy that is sufficient to physically delaminate or separate the graphene layer. As schematically illustrated, the graphene layer 114 is thereby released and separated from the template substrate 112. Following the delamination process the graphene layer 114 may be transferred to a target substrate as will be further described below.

The delamination process may include subjecting the template substrate 112 and the graphene layer 114 to electrochemical energy associated with an electrolysis reaction. The template substrate 112 and the graphene layer 114 may be submerged in a liquid or a solution comprising an electrolyte. The electrolyte may be an NaCl, NaOH or KOH solution. The concentration of the solution may be in the range of 0.05 to 5 M. The temperature of the electrolyte may be room temperature (e.g., 20° C.) or above.

After submerging the substrate 112 and the graphene layer 114, an electrolysis reaction may be caused in the liquid or the solution comprising the electrolyte. The electrolysis reaction may be caused in a number of ways. Generally, in an electrolysis reaction, a bias may be applied using a voltage source across a first electrode and a second electrode submerged in the liquid or the solution. In some embodiments, the first and second electrodes may be configured for the bias independent of the template substrate 112. In some other embodiments, when the template substrate 112 includes a conductor (such as Pt) the template substrate 112 may be connected to the voltage source and serve as a first electrode. A DC bias, e.g., a bias in the range of 1-20 V, may be applied. The DC bias may be applied until the graphene layer 114 has been delaminated from the template substrate 112. The DC bias may be applied for a duration in the range of few seconds to one or a few minutes, depending on for instance the magnitude of the DC bias.

The electrolysis results in an electrochemical reaction wherein bubbles of $O_2$ and $H_2$ form in the liquid or the solution including the electrolyte. Especially, bubbles form at the interface between the graphene layer 114 and the template substrate 112. The interfacial bubbles may cause the template substrate 112 and the graphene layer 114 to eventually release from each other. Without being bound to any theory, the mechanical energy transferred from surface tension of the bubbles generated by the electrolytic reaction may cause the template substrate 112 and the graphene layer 114 to be separated from each other.

The delamination process may alternatively include subjecting the template substrate 112 and the graphene layer 114 to ultrasound. The stack including the template substrate 112 and the graphene layer 114 may be submerged in a liquid. Ultrasonic signals may be induced in the liquid by an ultrasonic transducer. The ultrasonic signals may be ultrasonic pulses. By way of example, ultrasonic signals of a frequency between 30 kHz and 2 MHz may be applied for a duration of a few seconds to 30 minutes.

The stack including the template substrate 112 and the graphene layer 114 may be subjected to the ultrasound treatment until the graphene layer 114 has been delaminated from the template substrate 112.

Ultrasonic waves in the liquid medium will when incident on the graphene layer 114 and the template substrate 112 impart a momentum which may cause the template substrate 112 and the graphene layer 114 to be released from each other. Additionally, during a low pressure period of the soundwave, (vapor) bubbles may form at the interface between the graphene layer 114 and the template substrate 112. These bubbles may also contribute to separation of the template substrate 112 and the graphene layer 114.

Other delamination processes are also possible. For instance, the stack including the template substrate 112 and the graphene layer 114 may be submerged in $NH_4OH/H_2O_2/H_2O$ or in heated ammonium peroxide. According to another example, the stack including the template substrate 112 and the graphene layer 114 may be submerged in boiling water.

The water treatment and the delamination process may be performed in different containers or tanks. The stack including the template substrate 112 and the graphene layer 114 may accordingly be transferred from a first tank (for the water treatment) to a second tank, different from the first tank, (for the delamination process). It is however also possible to perform the water treatment and the delamination process in a same tank. If liquids with different properties are to be used in the water treatment and the delamination process (for instance if de-ionized or ultrapure water is to be used in the water treatment) the water may be evacuated from the tank following the water treatment and filled with another liquid (e.g., an electrolyte) before the delamination process is initiated.

Figure 2A:
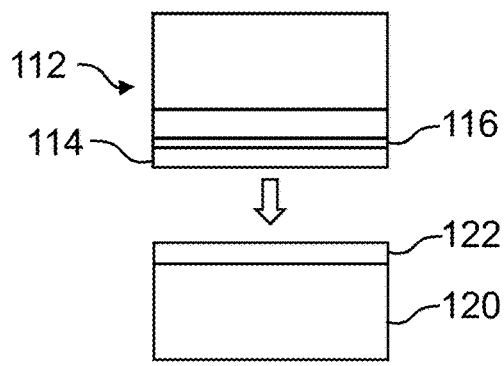
FIGS. 2a-2c are schematic illustrations of intermediate structures at various stages of a method of releasing a graphene layer from a template substrate and directly transferring and bonding the graphene layer to a target substrate, according to embodiments.
Figure 2B:
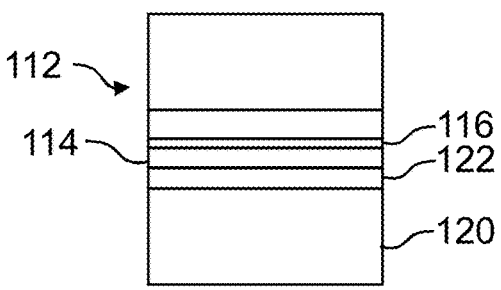
Figure 2C:
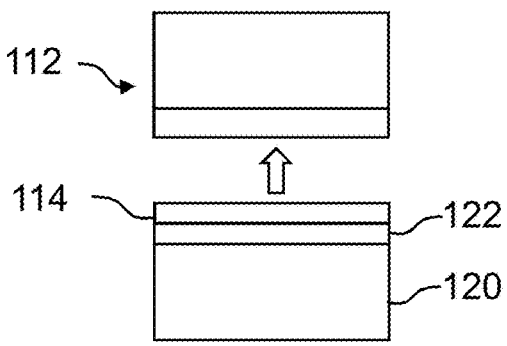

FIGS. 2a-2c schematically illustrates a method of releasing the graphene layer 114 from the template substrate 112 and directly transferring and bonding the graphene layer 114 to a target substrate 120.

As shown in FIG. 2a, a stack including the graphene layer 114, the template substrate 112 and intercalated water 116 forming IFW between the graphene layer 114 and the template substrate 112 is transferred to the target substrate 120. The state of the stack hence corresponds to what was described in connection with FIG. 1b above. Accordingly, the template substrate 112 and the graphene layer 114 are transferred to the target substrate 120 subsequent to the water treatment.

The target substrate 120 may be a semiconductor substrate. For example, the target substrate 120 may comprise Si or be a Si-substrate. A silicon oxide layer may be arranged on the Si-substrate. More generally, the target substrate 120 may be a bulk semiconductor substrate, a group IV semiconductor substrate (e.g., a Si-substrate or a Ge-substrate), a group III-V semiconductor substrate (e.g., a GaAs-substrate, an InGaAs-substrate, an InP-substrate), a silicon-on-insulator (SOI) substrate, a silicon-on-glass substrate, a silicon-on-sapphire substrate or a germanium-on-insulator-substrate (GeOI), to name a few examples. Partially completed devices of which the graphene layer 114 may form part may be present on the target substrate 120. The graphene layer 114 may also be arranged as an interconnect between already completed devices on the target substrate 120.

In some embodiments, the target substrate 120 may as shown be provided with a hydrophobic surface. The hydrophobic surface may comprise, e.g., a self-assembled monolayer (SAM) 122. In particular, the SAM 112 may have a tail group that is hydrophobic while having a head group that is adapted to bonding to silicon oxide. the SAM 112 may be formed using a suitable process, e.g., by vapor deposition. In one example, the SAM may be a layer of perfluorodecyl-trichlorosilane (FDTS). The terminal or tail group of a FDTS SAM is hydrophobic. The head group of a FDTS SAM allows bonding to a silicon oxide layer on a Si-substrate (or to a corresponding oxide layer if the target substrate 120 is formed by another semiconductor). An FDTS SAM is however only an example and any SAM with a hydrophobic tail group and a head group allowing bonding thereof to the target substrate 112 is possible, for instance octadecyl-trichlorosilane (ODTS) and hexamethyldisilazane (HMDS). However, it will be appreciated that the hydrophobic surface need not be provided by a SAM. For instance, a target substrate 120 of Si may be provided by a hydrophobic SiO$_2$. This can be obtained by a short dilute HF dip, or by an oven oxidation of Si.

In FIG. 2b, the stack including the template substrate 112 and the graphene layer 114 is subjected to a bonding process, wherein the graphene layer 114 is bonded to the target substrate 120, i.e., to the hydrophobic SAM 112 thereon.

In some embodiment, bonding may be achieved by a dry bonding process. A mechanical pressure on the order one to a few hundreds of kPa may be applied to the stack (in a normal direction to the layers of the stack). The pressure may be applied until the graphene layer 114 has bonded to the target substrate 120. The pressure may be applied for a duration in the range of one minute to one or a few tens of minutes. Other examples of bonding processes include vacuum bonding and anodic bonding.

After the graphene layer 114 has been bonded to the target substrate 120 (i.e. when the bonding process is completed) the graphene layer 114 and the template substrate 112 are subjected to the delamination process, wherein the graphene layer 114 is released from the template substrate 112. As shown in FIG. 2c, the graphene layer 114 and the template substrate 112 may thereafter be separated from each other while the graphene layer 114 remains bonded to the target substrate 120. By virtue of the hydrophobic surface of the target substrate 120 provided by the SAM 122, water intercalation between the target substrate 120 and the graphene layer 114 during the water treatment may be counteracted.

Following the stage of the method as illustrated by the intermediate structure shown in FIG. 2c, further processing may be performed for forming devices and circuits making use of the graphene layer 114 on the substrate 120.

In the method shown in as shown in FIGS. 2a-2c, the water treatment, the bonding process and the delamination process are performed in a sequential and non-overlapping manner. However, at least the following variations however possible:

According to one variation, the stack including the graphene layer 114 and the template substrate 112 may, directly following the growth process, be transferred to the target substrate 120. The bonding process may thereafter be performed wherein the graphene layer 114 is bonded to the target substrate 120. Subsequent to the bonding, the stack including the target substrate 120, the SAM 122 (if present), the graphene layer 114 and the template substrate 112 may be soaked in water such that water is intercalated between the template substrate 112 and the graphene layer 114, as described above. Subsequent to the water treatment, the delamination process may be performed, causing the release of the graphene layer 114 from the template substrate 112.

According to another variation, the bonding process may even be performed during (e.g., at least partially temporally overlap with) the water treatment. A mechanical pressure may be applied to the stack including the target substrate 120, the SAM 120 (if present), the graphene layer 114 and the template substrate 112, while the stack is being soaked.

According to another variation, the delamination process may be performed during (i.e. at least partially overlap with) the bonding process. A mechanical pressure may be applied to the stack including the target substrate 120, the SAM 120 (if present), the graphene layer 114 and the template substrate 112, while the delamination process, for instance by electrolysis, is performed. The mechanical pressure may for instance be released after completion of the electrolysis.

Figure 5A:
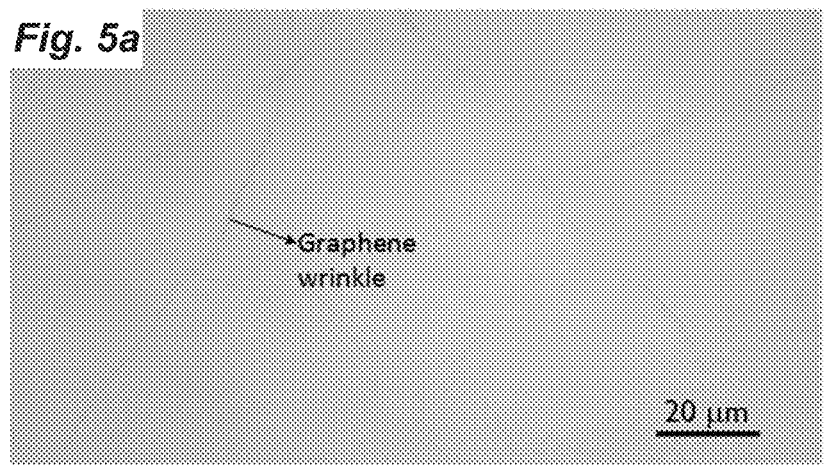
FIGS. 5a-5b are SEM images of a graphene layer after it has been transferred and bonded to a target substrate.
Figure 5B:
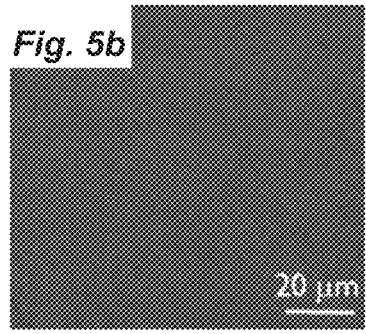
Figure 5C:
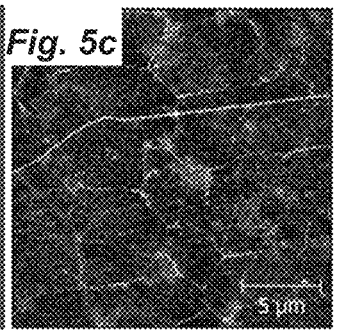
FIG. 5c is an atomic force microscope (AFM) image of a graphene layer after it has been transferred and bonded to a target substrate.

FIGS. 5a-5b illustrate scanning electron microscope (SEM) images and FIG. 5c illustrates an atomic force microscope (AFM) image of a graphene layer 114 after it has been has been transferred and bonded to a target substrate 120. In a first step, an Al$_2$O$_3$/Pt/graphene layer sample stack was immersed in ultra-pure water at 50° C. for 16 h to achieve water intercalation between the graphene layer and the Pt(111) surface.

Next, a Si/SiO$_2$ target substrate coated with a FDTS SAM was bonded to the Al$_2$O$_3$/Pt(111)/IFW/graphene layer sample stack by applying a pressure of 200 kPa to the sample stack. Next, electrolysis was performed by applying a −2.5 V voltage for 2 min to the sample stack submerged in an 0.2 M NaOH electrolyte. The aqueous NaOH was thereafter rinsed off with UPW until the pH of the solution reached 7 and finally the pressure applied to the sample stack was gradually removed.

FIGS. 5a-5c illustrate the feasibility of a direct graphene layer transfer method from a template substrate to a target substrate. The SEM and AFM images show the presence of wrinkles in the graphene layer. Those wrinkles may, however, be attributed to the graphene growth process, since the thermal expansion coefficient of graphene and Pt are different (wrinkles appear during cool down after growth) and not to the delamination, transfer and bonding processes.

The inventors have obtained a Raman map using space-resolved Raman spectroscopy. The Raman map of the graphene layer after the transfer process showed a full-width-half-maximum (FWHM) of the 2D peak of $\Gamma_{2D}=27.3\pm2.2$ cm$^{-1}$, and a 2D/G peak ratio of $1.22\pm0.11$. Without being bound to any theory, the $\Gamma_{2D}$ peak has been associated with strain inhomogeneities on a nanometer length scale in the graphene sheet. A direct correlation between the carrier mobility and $\Gamma_{2D}$ has been shown. As a result, $\Gamma_{2D}$ may be an easily accessible quantity for classifying nanometer scale flatness as well as the local electronic properties of a graphene layer. The small value of $\Gamma_{2D}$ in the Raman maps is a good indication of the virtues of the transfer process. Annealing the sample at 150° C. for 1 h in a nitrogen atmosphere decreases the 2D/G peak ratio to $1.08\pm0.11$ while $\Gamma_{2D}$ remains almost identical. After annealing, graphene doping is higher likely due to stronger interaction between the FDTS SAM and the graphene. A lower 2D/G ratio shows a higher doping. The FWHM does not change significantly, so the graphene mobility is not expected to be impacted by the anneal step.

The results shown in FIGS. 4a-4d and 5a-5c were obtained using a SEM (FEI Nova 200) and an AFM (Bruker Dimension Edge). The Raman spectroscopy was performed using a Raman spectrometer (Horiba Labram HR) with a green laser ($\lambda$=532 nm) and a grating of 600 gr/mm.

Figure 3A:
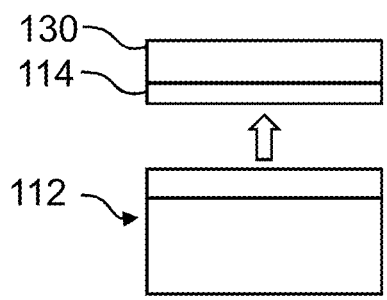
FIGS. 3a-3c are schematic illustrations of intermediate structures at various stages of a method of releasing a graphene layer from a template substrate and subsequently transferring and bonding the graphene layer to a target substrate, according to embodiments.
Figure 3B:
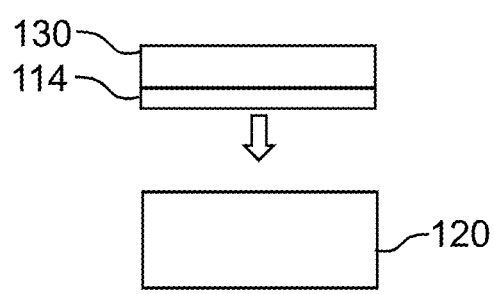
Figure 3C:
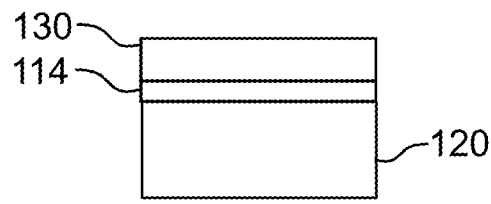

FIGS. 3a-3c are schematic illustrations of intermediate structures at various stages of fabrication according to a method of releasing the graphene layer 114 from the template substrate 112 and subsequently transferring and bonding the graphene layer 114 to a target substrate 120. FIG. 3a corresponds to the stage of the method shown in FIG. 1c wherein the graphene layer 114 has released from the template substrate 112 and been separated therefrom.

A carrier layer 130 is formed on the first surface of the graphene layer 114 facing away from the template substrate 112. The carrier layer 130 may be formed either prior to or subsequent to the water treatment. The carrier layer 130 may be a polymer-including layer. The carrier layer 130 may be a spin-coated organic layer. The carrier layer 130 may be a polymethyl-methacrylate (PMMA) spin-coated layer. The carrier layer 130 may be a stack of a polydimethylsiloxane (PDMS) layer and a PMMA layer, with the PMMA layer closest to the graphene layer 114. The carrier layer 130 may however also be other types of organic layers, for instance of polystyrene, polypropylene or a thermal release tape to name a few examples.

In FIG. 3b, the graphene layer 114 and the carrier layer 130 are transferred to the target substrate 120, with the first surface of the graphene layer 114 facing a main surface of the target substrate 120. For details of the target substrate 120, reference is made to the above detailed discussion in connection with FIG. 2a-c.

In FIG. 3c, the graphene layer 114 has been bonded to the target substrate 120. The bonding may be achieved for instance by a dry bonding process as described in connection with FIGS. 2a-2c. Adhesive bonding techniques may however also be employed. Other examples of bonding processes include vacuum bonding and anodic bonding. Subsequent to the bonding, the carrier layer 130 may be removed from the graphene layer 114, which remains on the target substrate 120. Depending on the type of carrier layer, the carrier layer 130 may be removed by mechanical peeling, polishing and/or solvents. Spin-coated organic layers may be dissolved in room temperature acetone bath.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, it is possible to, instead of the "water treatment" subject the graphene layer and the template substrate to a liquid treatment by soaking the graphene layer and the template substrate in a liquid such that liquid is intercalated between the template substrate and the graphene layer. The liquid may (as described above) include water, however other liquids such as chloroform may also be used. The above described methods may be performed in a similar manner also in the case of soaking the graphene layer and the template substrate in another liquid than water. The delamination process may for instance include submerging the stack including the template substrate, the intercalated liquid and the graphene layer into an electrolyte and performing an electrolysis step.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of releasing a graphene layer formed on a template substrate, the method comprising:
    soaking the graphene layer and the template substrate in water such that water is intercalated between the template substrate and the graphene layer; and
    delaminating the graphene layer from the template substrate, thereby releasing the graphene layer.

2. The method according to claim 1, wherein soaking is performed for a predetermined duration prior to delaminating.

3. The method according to claim 2, wherein soaking is performed for at least 1 hour.

4. The method according to claim 1, wherein soaking comprises soaking in water at a temperature of at least 30° C.

5. The method according to claim 1, further comprising:
    prior to delaminating, transferring the template substrate and the graphene layer to a target substrate and bonding the graphene layer to the target substrate,
    wherein delaminating comprises releasing the graphene layer from the template substrate while keeping the graphene layer bonded to the target substrate.

6. The method according to claim 5, wherein bonding comprises bonding the graphene layer to a hydrophobic surface of the target substrate.

7. The method according to claim 6, wherein the hydrophobic surface comprises a self-assembled monolayer (SAM) formed on the target substrate.

8. The method according to claim 7, wherein the SAM is a monolayer selected from the group consisting of perfluorodecyltrichlorosilane (FDTS), octadecyltrichlorosilane (ODTS) and hexamethyldisilazane (HMDS).

9. The method according to claim 1, further comprising:
forming a carrier layer on a second surface of the graphene layer facing away from the template substrate; and
subsequent to releasing the graphene layer from the template substrate, transferring and bonding the graphene layer to a target substrate with a first surface of the graphene layer facing the target substrate.

10. The method according to claim 1, wherein delaminating includes submerging the template substrate and the graphene layer in a liquid and forming bubbles at an interface between the template substrate and the graphene layer.

11. The method according to claim 1, wherein delaminating includes submerging the template substrate and the graphene layer in a solution comprising an electrolyte and causing an electrolysis reaction.

12. The method according to claim 11, wherein the electrolysis reaction is caused by applying a voltage between two electrodes, wherein the template substrate serves as one of the electrodes.

13. The method according to claim 1, wherein delaminating includes subjecting the template substrate and the graphene layer to ultrasound.

14. The method according to claim 1, further comprising providing the graphene layer formed on the template substrate, wherein providing the graphene layer comprises growing on the template substrate.

15. The method according to claim 1, wherein the template substrate comprises a surface formed of one of a transition metal, an alloy of transition metals, a group III element or a group IV element.

16. The method according to claim 15, wherein the surface of the template substrate is formed of Pt.

17. The method according to claim 1, wherein the template substrate includes a growth layer on which the graphene layer is provided and a support layer on which the growth layer is arranged.

* * * * *